(12) United States Patent
Sonezaki et al.

(10) Patent No.: US 8,431,143 B2
(45) Date of Patent: Apr. 30, 2013

(54) THERAPEUTIC METHOD OF ADMINISTERING PHARMACEUTICAL TITANIUM DIOXIDE COMPOSITE AND LIGHT IRRADIATION

(75) Inventors: Shuji Sonezaki, Kitakyushu (JP); Koki Kanehira, Kitakyushu (JP); Yumi Ogami, Yukuhashi (JP); Toshiaki Banzai, Kitakyushu (JP); Yoshinobu Kubota, Yokohama (JP)

(73) Assignee: Toto Ltd., Fukuoka-ken (JP)

( * ) Notice: Subject to any disclaimer, the term of this patent is extended or adjusted under 35 U.S.C. 154(b) by 261 days.

(21) Appl. No.: 12/889,753

(22) Filed: Sep. 24, 2010

(65) Prior Publication Data

US 2011/0014245 A1 Jan. 20, 2011

Related U.S. Application Data

(62) Division of application No. 11/990,040, filed as application No. PCT/JP2006/315499 on Aug. 4, 2006, now abandoned.

(30) Foreign Application Priority Data

Aug. 5, 2005 (JP) .................................. 2005-228015
Jun. 21, 2006 (JP) .................................. 2006-171781

(51) Int. Cl.
| | |
|---|---|
| A61P 33/00 | (2006.01) |
| A61K 47/48 | (2006.01) |
| A61K 9/00 | (2006.01) |
| A61K 9/14 | (2006.01) |
| A61K 9/16 | (2006.01) |
| A61K 31/70 | (2006.01) |
| A61K 9/10 | (2006.01) |
| A61K 31/704 | (2006.01) |
| A61K 47/02 | (2006.01) |
| A01N 25/32 | (2006.01) |
| A01N 43/04 | (2006.01) |

(52) U.S. Cl.
USPC ........... 424/406; 424/400; 424/486; 424/487; 424/488; 424/489; 424/490; 514/34; 977/903; 977/904; 977/905; 977/906; 977/911; 977/915

(58) Field of Classification Search ....................... None
See application file for complete search history.

(56) References Cited

U.S. PATENT DOCUMENTS 5,330,760 A * 7/1994 Walton .......................... 424/466
5,412,072 A 5/1995 Sakurai et al.
(Continued)

FOREIGN PATENT DOCUMENTS

| JP | 2-300133 A | 12/1990 |
|---|---|---|
| JP | 5-000955 A | 1/1993 |

(Continued)

OTHER PUBLICATIONS

Sweetman, Sean C.; "Martindale: The Complete Drug Reference", 33$^{rd}$ ed. 2002, Pharmaceutical Press, pp. 511-513 and 534-536.*

(Continued)

Primary Examiner — Cherie M Stanfield
Assistant Examiner — Ivan Greene
(74) Attorney, Agent, or Firm — Carrier Blackman & Associates, P.C.; Joseph P. Carrier; William D. Blackman

(57) ABSTRACT

A titanium dioxide composite is provided that can be stably dispersed in an aqueous solvent and easily administered into a living body, such as human, and allows elimination of the drug efficacy of a pharmaceutical compound supported thereon by light irradiation and a dispersion thereof. A composite is used in which a pharmaceutical compound is bound to titanium dioxide having photocatalytic activity through a hydrophilic polymer. The composite is stable in an aqueous solvent and easily administered into a living body, and adverse drug reactions of the pharmaceutical compound can be reduced by administering the composite into the body and irradiating the composite with a light to photoexcite the titanium dioxide to decompose the pharmaceutical compound in a region where the drug efficacy of the pharmaceutical composition is not required.

4 Claims, 2 Drawing Sheets

U.S. PATENT DOCUMENTS

| | | | |
|---|---|---|---|
| 5,783,178 A | | 7/1998 | Kabanov et al. |
| 6,462,017 B1* | | 10/2002 | Rudolph et al. ............... 514/9.7 |
| 2004/0179978 A1 | | 9/2004 | Kobayashi et al. |
| 2004/0248075 A1* | | 12/2004 | Yamaguchi et al. ............... 435/2 |
| 2005/0079219 A1* | | 4/2005 | Christenson et al. ......... 424/468 |
| 2006/0264520 A1* | | 11/2006 | Sonezaki et al. ................ 516/90 |
| 2006/0281087 A1 | | 12/2006 | Sonezaki et al. |

FOREIGN PATENT DOCUMENTS

| | | | |
|---|---|---|---|
| JP | 7-069900 A | | 3/1995 |
| JP | 2002-316946 A | | 10/2002 |
| JP | 2002-316950 A | | 10/2002 |
| WO | 03-033143 A1 | | 4/2003 |
| WO | 03-033145 A1 | | 4/2003 |
| WO | 2004/087577 A1 | | 10/2004 |
| WO | 2004-087577 A1 | | 10/2004 |
| WO | WO 2004087577 A1 * | | 10/2004 |

OTHER PUBLICATIONS

Warmer, Wayne G. et al.; "Oxidative Damage to Nucleic Acids Photosensitized by Titanium Dioxide", 1997, Elsevier, Free Radical Biology & Medicine, vol. 23, No. 6, pp. 851-858.*

Dictionary.com® entry for "chemotherapy", retrieved from <dictionary.reference.com> on Mar. 25, 2011, pp. 1-4.*

The Batte Cancer Center, Northeast Medical Center: "The Chemotherapy Experience", retrieved from <cmc-northeastorg/workfiles/PDFs/TheChemotherapyExperience.pdf> on Mar. 26, 2011, pp. 1-7.*

Stedman's Medical Dictionary, 27$^{th}$ ed., 2000, Lippincott Williams & Wilkins, entry for "lesion", p. 1.*

Sweetman, Sean C.; "Martindale: The Complete Drug Reference", 33rd ed. 2002, Pharmaceutical Press, pp. 511-513 and 534-536.*

Mills, Andrew and Le Hunte, Stephen; "An overview of semiconductor photocatalysis", 1997, Elsevier, Journal of Photochemistry and Photobiology A: Chemistry, vol. 108, pp. 1-35.*

Warmer, Wayne G. et al.; "Oxidative Damage to Nucleic Acids Photosensitized by Titanium Dioxide", 1997, Elsevier, Fre Radical Biology & Medicine, vol. 23, No. 6, pp. 851-858.*

Thakrar, Nutan and Douglas, Kenneth Thomas; "Photolability of Bleomycin and Its Complexes", 1981, Elsevier, Cancer Letters, vol. 13, pp. 265-268.*

Dictionary.com® entry for "chemotherapy", retrieved from on Mar. 25, 2011, pp. 1-4.*

Merriam-Webster's Collegiate Dictionary, 11 th ed., entry for "antibiotic", Merriam-Websters Inc., 2004, pp. 1-20.*

Stedman's Medical Dictionary, 27med., 2000, Lippincott Williams & Wilkins, entry for "tumor", p. 1.*

* cited by examiner

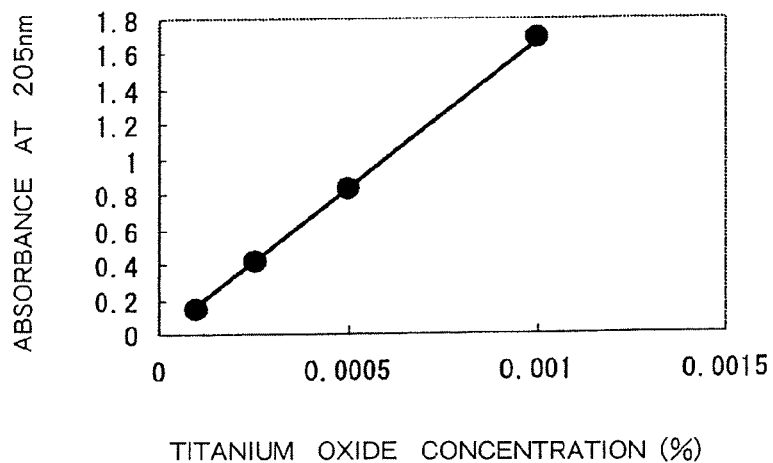
F I G. 1
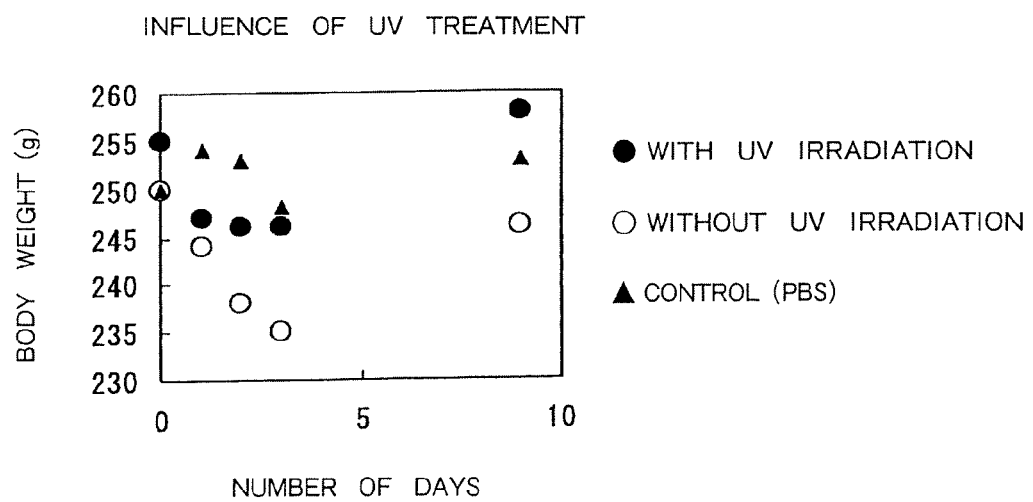
F I G. 2

THERAPEUTIC METHOD OF ADMINISTERING PHARMACEUTICAL TITANIUM DIOXIDE COMPOSITE AND LIGHT IRRADIATION

CROSS-REFERENCE TO RELATED APPLICATIONS

The present application is a Divisional application of U.S. Ser. No. 11/990,040, filed on 5 Feb. 2008 (now abandoned), which is a U.S. National phase of, and claims priority based on PCT/JP2006/315499, filed 4 Aug. 2006, which, in turn, claims priority from Japanese patent application 2005-228015, filed 5 Aug. 2005, and Japanese patent application 2006-171781, filed 21 Jun. 2006. The entire disclosure of each of the referenced priority documents is incorporated herein by reference.

BACKGROUND OF THE INVENTION

1. Technical Field

The present invention relates to a composite comprising titanium dioxide having photocatalytic activity and a pharmaceutical compound having drug efficacy, and particularly relates to a titanium dioxide composite with which a pharmaceutical compound is decomposed by photoexcitation of titanium dioxide to lose drug efficacy thereof. More particularly, the present invention relates to a method of treating a lesion by administering a dispersion to an animal including human, and subsequently irradiating a region surrounding the lesion.

2. Background Art

It is well known that a redox reaction occurs upon photoexcitation of titanium dioxide. In addition, titanium dioxide is used for foods and its safety has been confirmed to a certain level. It has been attempted that such titanium dioxide is administered in vivo to utilize its photocatalytic activity.

For example, WO2004/087765 proposes a titanium dioxide composite in which a molecule having molecular recognition ability binds to titanium dioxide through a hydrophilic polymer. It is attempted that this composite is introduced in a living body, then collected in a specific tissue or cells in the body by the molecule having molecular recognition ability, and irradiated with light to destroy the tissue or cells by the redox power of titanium dioxide. However, this WO publication does not disclose or suggest destruction of a molecule having molecular recognition ability itself supported in the composite by the redox power of titanium dioxide.

On the other hand, since some pharmaceutical compounds having specific drug efficacy such as anticancer drugs are often accompanied by adverse drug reactions, there is a technique with which a pharmaceutical compound is delivered only to an affected lesion but not to other healthy tissues or cells. This is a so-called drug delivery system (DDS) technique.

For example, for adriamycin, an anticancer drug, Japanese Patent Application Laid-Open Publication No. 7-69900, Japanese Patent Application Laid-Open Publication No. 5-955, Japanese Patent Application Laid-Open Publication No. 2-300133, and the like describe techniques combined with a polymer. However, improvement is still required in terms of efficient delivery to cancer cells, further suppression of adverse drug reactions and the like.

Further, Japanese Patent Application Laid-Open Publication No. 2002-316946 and Japanese Patent Application Laid-Open Publication No. 2002-316950 disclose a technique in which a drug, especially adriamycin, is supported on metal particles coated with titanium dioxide having photocatalytic activity and then introduced into cancer cells by a gene gun. It is said that when a drug is desired to be detoxified, the drug can be decomposed by a photocatalyst by UV irradiation in this technique. Since this technique premises the use of a gene gun, a special device, and a drug is supported by simple physical adsorption, however, there is room for improvement in terms of versatility and stability.

SUMMARY OF THE INVENTION

The present inventors have now found that a composite in which a pharmaceutical compound binds to titanium dioxide having a photocatalytic activity through a hydrophilic polymer is stable in an aqueous solvent and easy to be administered into a living body and that adverse drug reactions of the pharmaceutical compound can be reduced by administering the composite into the living body and irradiating the composite with a light to photoexcite titanium dioxide to decompose the pharmaceutical compound in the regions where the drug efficacy of the pharmaceutical composition is not required. The present invention is based on these findings.

Accordingly, an object of the present invention is to provide a titanium dioxide composite that can be stably dispersed in an aqueous solvent, easily be administered into the body and allow drug efficacy of a pharmaceutical compound supported therein to disappear by light irradiation. It is also an object of the present invention to provide a dispersion thereof.

Accordingly, the titanium dioxide composite according to the present invention comprises a titanium dioxide particle, a hydrophilic polymer bonded to the surface of the titanium dioxide particle, and a pharmaceutical compound having a desired drug efficacy and bonded to the hydrophilic polymer, wherein the pharmaceutical compound is decomposed by photoexcitation of the titanium dioxide to allow the drug efficacy to disappear.

Further, the dispersion according to the present invention comprises the titanium dioxide composite dispersed in an aqueous solvent, and this dispersion is used in a method comprising the steps of administering the dispersion to an animal, and subsequently irradiating with UV light a region other than the lesion at least surrounding the lesion, without irradiating the lesion, to photoexcite titanium dioxide in the titanium dioxide composite contained in the dispersion, so that a pharmaceutical compound is decomposed by photoexcitation of the titanium dioxide to allow the drug efficacy to disappear.

Further, the method of treating a lesion according to the present invention comprises the steps of administering the dispersion to an animal including human, and subsequently irradiating with UV light a region other than the lesion at least surrounding the lesion, without irradiating the lesion, to photoexcite titanium dioxide in a titanium dioxide composite contained in the dispersion, so that a pharmaceutical compound is decomposed by photoexcitation of the titanium dioxide to allow the drug efficacy to disappear.

Further, the use according to the present invention is use of the titanium dioxide composite in the manufacture of a agent for treating a lesion, wherein the agent for treating the lesion is used in a method comprising the steps of administering the agent for treating the lesion to an animal including human, and subsequently irradiating with UV light a region other than the lesion at least surrounding the lesion, without irradiating the lesion, to photoexcite titanium dioxide in a titanium dioxide composite contained in the agent for treating the lesion, so that a pharmaceutical compound is decomposed by photoexcitation of the titanium dioxide to allow the drug efficacy to disappear.

BRIEF DESCRIPTION OF THE DRAWINGS

FIG. 1 shows the relationship between the titanium oxide content of a nanoparticle dispersion liquid of polyacrylic acid-coated titanium oxide prepared in Example 1 and absorption of UV light.

FIG. 2 shows changes in body weight of mice injected with a dispersion liquid of titanium oxide nanoparticles coated with polyacrylic acid on which adriamycin is immobilized prepared in Example 3 into oral tissue depending on the presence/absence of UV light irradiation.

DETAILED DESCRIPTION OF THE INVENTION

Figure 3:
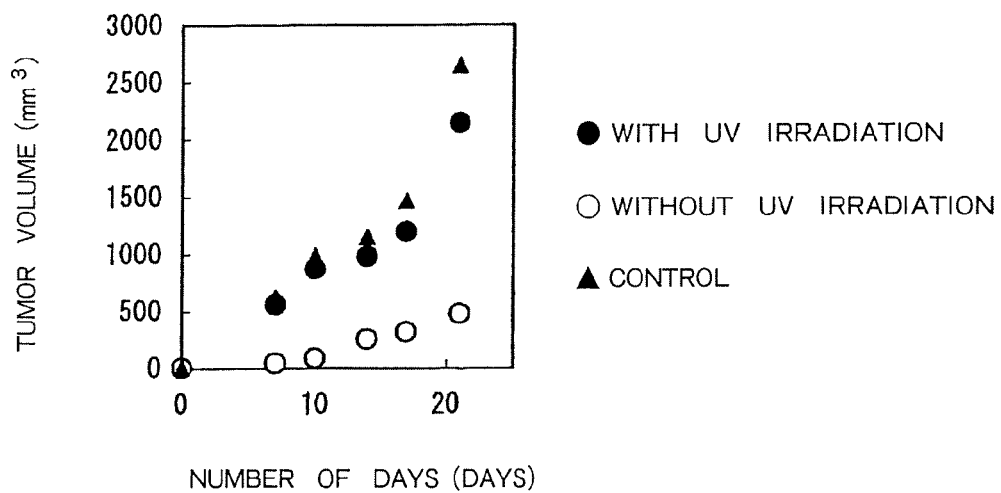
FIG. 3 shows the test results of an antitumor effect of titanium oxide nanoparticles coated with polyacrylic acid on which adriamycin is immobilized in Example 6.

The titanium dioxide composite according to the present invention basically comprises titanium dioxide, a hydrophilic polymer bonded to the surface of the titanium dioxide, and a pharmaceutical compound having a desired drug efficacy and bonded to the hydrophilic polymer.
Titanium Dioxide The titanium dioxide constituting the composite according to the present invention is not particularly limited as long as it has a photocatalytic activity, and may be, for example, either an anatase type or a rutile type. Since the anatase type generally has a greater photocatalytic activity than the rutile type, the anatase type is preferably used.

In the present invention, although the particle size of the titanium dioxide particle may be appropriately selected, considering that the particles are difficult to be aggregated and the particles are introduced into the body. According to a preferred embodiment of the present invention, the particle size is preferably 2 to 200 nm, and further preferably about 50 to about 200 nm when its accumulation in body tissues, especially in cancer cells, is desired.

According to one embodiment of the present invention, the titanium dioxide particle of the present invention may be combined with another material as long as the titanium dioxide is present on at least part of the surface of a particle and exhibits photocatalytic activity. For example, the titanium oxide particle may be a composite of a magnetic material and titanium dioxide.
Hydrophilic Polymer The hydrophilic polymer used in the present invention is preferably water soluble and has both a functional group capable of bonding to the surface of a titanium dioxide particle and a functional group capable of bonding to a pharmaceutical compound having a drug efficacy described below. In addition, this hydrophilic polymer preferably has both a function to stably disperse the titanium dioxide particle in water and a characteristic to provide an appropriate pH as described below.

The hydrophilic polymer is not limited in terms of structure, molecular weight, or the like, as long as it satisfies the above requirements. According to the preferred embodiment of the present invention, however, the hydrophilic polymer preferably has a plurality of carboxyl groups. Preferred examples thereof include carboxymethyl starch, carboxymethyl dextran, carboxymethyl cellulose, polycarboxylic acids and copolymers having carboxyl groups. More specifically, polycarboxylic acids such as polyacrylic acid and polymaleic acid, and copolymers of acrylic acid/maleic acid and acrylic acid/sulfonic acid monomers, and the like are more suitably used from the viewpoint of hydrolyzability and solubility of the water-soluble polymer. According to a preferred embodiment of the present invention, the molecular weight of the hydrophilic polymer is preferably about 2,000 to about 100,000, and more preferably its lower limit is about 5,000 and its upper limit is about 30,000.

The hydrophilic polymer can be bonded to the surface of the titanium dioxide particle by a reaction between the functional group of the hydrophilic polymer and a hydroxyl group generated on the surface of the titanium oxide particle by hydration of titanium oxide with water in the reaction system. When the hydrophilic polymer has a carboxyl group, for example, the titanium dioxide particles and the hydrophilic polymer may be dispersed in dimethylformamide and a hydrothermal reaction may be performed at 90 to 180° C. for 1 to 12 hours to bond them through an ester bond. The ester bond can be confirmed by various analytical methods, and for example, according to the presence of infrared absorption at around 1700 to 1800 $cm^{-1}$ that is an absorption band of an ester bond by the infrared absorption spectrophotometry.
Pharmaceutical Compound The pharmaceutical compound used in the present invention is a compound having a predetermined drug efficacy and used for the treatment or prevention of an established disease. The present invention is advantageously applied to a pharmaceutical compound that causes severe adverse drug reactions and is thus desired to be delivered only to cells or tissue to be treated as much as possible.

Specific examples of the pharmaceutical compound that can be used in the present invention includes anticancer drugs, for example, antimetabolites (such as 5-fluorouracil, doxifluridine, UTF, methotrexate), antitumor antibiotics (such as doxorubicin, mitomycin C, bleomycin, adriamycin), gold derivatives (cisplatin, nedaplatin), alkylating agents (such as cyclophosphamide), topoisomerase inhibitors (such as irinotecan, etoposide), and plant alkaloids (such as taxol).

For hydrophobic pharmaceutical compounds, especially anticancer drugs most of which are hydrophobic, this hydrophobicity advantageously makes uptake of the titanium dioxide composite into cells efficient. Especially, as described above, when the particle size of the titanium dioxide particles is suitable for their accumulation in cancer cells, the hydrophobicity has an advantage that the titanium dioxide composite according to the present invention can be efficiently accumulated in cancer cells.

In the titanium dioxide composite according to the present invention, a pharmaceutical compound is bonded by a reaction of a functional group of the hydrophilic polymer bonded to the surface of the titanium dioxide particle with a functional group of the pharmaceutical compound. Functional groups involved in the bonding between them may be appropriately selected. When a hydrophilic polymer has a carboxyl group, a pharmaceutical compound preferably has an amino group, aldehyde group, or the like. Even if a pharmaceutical compound has no such appropriate functional group, an appropriate functional group can be introduced to bond the pharmaceutical compound to a hydrophilic polymer, as far as the introduction does not affect drug efficacy. Such a pharmaceutical compound bonded to a hydrophilic polymer through a functional group is particularly preferable, since the compound is stably supported by the titanium dioxide particle and does not detach or diffuse before it reaches a lesion when it is administered into the body of an animal as described below.

Further, the titanium dioxide composite according to the present invention is constituted such that a pharmaceutical compound is decomposed by a redox reaction caused by photoexcitation of titanium dioxide to allow the drug efficacy thereof to disappear.

In the present invention, when a pharmaceutical compound bonds to a water-soluble polymer through a functional group thereof, one functional group is lost theoretically. For example, when a functional group of a water-soluble polymer involved in bonding is a carboxyl group, loss of the carboxyl group due to bonding to a pharmaceutical compound may affect its water solubility and thus may affect dispersibility of the titanium dioxide composite. In a certain embodiment of the present invention, it is thus necessary to appropriately keep balance between bonding to a pharmaceutical compound and water solubility of a water-soluble compound and further dispersibility of titanium dioxide. For example, a titanium oxide-polyacrylic acid composite having a particle size of 2 to 200 nm in which a pharmaceutical compound is adriamycin and a water soluble polymer is polyacrylic acid has about 1 to about 1.000 mmol of free carboxylic groups per gram of titanium oxide. Here, although bonding of a pharmaceutical compound involves activation and substitution of this functional group, loss of about 1% of the carboxylic group does not appear to substantially affect dispersibility. Therefore, according to this embodiment, adriamycin can be bonded to about 1/100 to about 1/1,000 of the carboxyl groups. According to a preferred embodiment of the present invention, the amount of adriamycin bound can be about 0.001 to about 100 mg and is preferably about 0.1 to 10 mg, more preferably about 0.5 to about 5 mg per gram of titanium dioxide.

Titanium Dioxide Composite Dispersion and Therapeutic Method Using the Same

The titanium dioxide composite according to the present invention is stably dispersible in an aqueous solvent due to hydrophilicity of the hydrophilic polymer. According to a preferred embodiment of the present invention, when a hydrophilic polymer has a carboxyl group, it is considered that a repulsive force derived from a negative charge of the carboxyl group acts between the composites in an aqueous solvent and the composites are thus stably dispersed. The titanium dioxide composite according to the present invention can be stably present in an aqueous solvent in a wide pH range, and for example, a homogenously dispersed state without aggregation can be maintained at pH 3 to 13.

Accordingly, the titanium dioxide composite according to the present invention can be made into a form of homogenous and stable dispersion liquid in water, buffers at various pHs, infusion liquid, physiological saline solution, etc. Since this dispersion liquid is not likely to aggregate even under near-neutral physiological conditions, a stable oral or parenteral dosage form can be provided. Particularly, this dispersion liquid can be administered to an animal through an injection preparation that is injected directly to a lesion or by intravenous injection, without requiring a special device or the like. An ointment or a spray preparation containing this dispersion liquid can also be applied directly onto a lesion such as the skin. The dosage form thereof may be appropriately determined taking into consideration a type of a pharmaceutical compound and a disease and a lesion to be treated, and the dispersion according to the present invention is advantageously applicable to a variety of dosage forms. Further, according to the present invention, an administration route that allows concentration and accumulation of the titanium dioxide composite in a lesion is preferable.

According to the present invention, after administration of the titanium dioxide composite into the body, preferably, titanium dioxide composite is concentrated and accumulated in a lesion and then UV light is irradiated not on the lesion but on a region other than the lesion at least surrounding the lesion. Titanium dioxide is photoexcited by the light irradiation and exhibits redox power. The redox power decomposes a pharmaceutical compound supported on the composite. As a result, drug efficacy of the pharmaceutical compound disappears, and at the same time, adverse drug reactions are also eliminated. According to the present invention, drug efficacy of a pharmaceutical compound can be thus exhibited only at a lesion requiring treatment and influence of the pharmaceutical compound can be eliminated in the other regions where the pharmaceutical compound is not required.

In the present invention, although light for photoexcitation of titanium dioxide is not particularly limited as long as the light can cause photoexcitation of titanium dioxide, its wavelength is preferably 400 nm or less and UV light having a wavelength of 280 nm is more preferable in relation to a band gap of titanium dioxide. Specific light source and apparatus for irradiation may be appropriately determined, selected, and designed. When light is irradiated through the skin, sunlight, an ordinary UV lamp, a black light, and the like can be preferably used. When light is irradiated directly to a lesion inside the body, for example, a UV fiber is mounted to an endoscope for light irradiation.

According to a preferred embodiment of the present invention, treatment can be conducted using an anticancer drug, especially adriamycin, as a pharmaceutical compound, and targeting a cancer tissue as a lesion.

EXAMPLES

The present invention will be described in more detail referring to the following Examples, but the present invention is not limited to these Examples.

Example 1

Preparation of a Dispersion of Titanium Oxide Nanoparticles Coated with Polyacrylic Acid An aliquot of 3.6 g titanium tetraisopropoxide and 3.6 g of isopropanol were mixed and the resultant mixture was added dropwise to 60 ml of ultrapure water under ice cooling to perform hydrolysis. After dropwise addition, the mixture was stirred at room temperature for 30 minutes. After stirring, 1 mL of 12 N nitric acid was added dropwise, and the resultant mixture was stirred at 80° C. for 8 hours for peptization. After the completion of peptization, the mixture was filtered through a 0.45 μm filter and subjected to solution exchange using a desalting column (PD10, Amersham Pharmacia Bioscience) to prepare an anatase-type titanium dioxide sol having a solid content of 1%.

The dispersion liquid was placed in a 100 mL vial bottle and subjected to ultrasonic treatment at 200 Hz for 30 minutes. The average particle sizes of the dispersion liquid before and after ultrasonic treatment were 36.4 nm and 20.2 nm, respectively. After the ultrasonic treatment, the solution was concentrated to prepare an anatase-type titanium dioxide sol having a solid content of 20%.

An aliquot of 0.75 mL of the anatase-type titanium dioxide sol thus obtained was dispersed in 20 mL of dimethylformamide (DMF), and 10 mL of DMF containing 0.3 g of polyacrylic acid (average molecular weight: 5,000, Wako Pure Chemical Industries, Ltd.) dissolved therein was added and mixed by stirring. The solution was transferred into a hydrothermal reaction vessel (HU-50, SAN-AI Science Co., Ltd.), and synthesis was performed at 150° C. for 5 hours. After the completion of the reaction, the vessel was cooled until the temperature of the vessel was 50° C. or lower. The solution was removed, then 60 mL of isopropanol was added, and the resultant mixture was centrifuged at 4000×g for 20 minutes after left standing for 1 hour. The sediment was collected and washed with 70% ethanol, then distilled water was added to prepare a polyacrylic acid-coated titanium oxide nanoparticle dispersion liquid.

Absorption spectrophotometry showed that this dispersion liquid had absorption peaks at wavelengths of 205 nm and 250 nm. The absorbance at the peaks at both of the wavelengths showed a close correlation with the measured titanium oxide contents obtained by the ash analysis of this dispersion liquid. The content of titanium oxide of the dispersion liquid was thus quantified by measurement of UV absorption. The results are as shown in FIG. 1.

Example 2

Preparation of a Dispersion Liquid of Titanium Oxide Nanoparticles Coated with Polyacrylic Acid on which Adriamycin is Immobilized Water was added to the titanium oxide nanoparticles coated with polyacrylic acid prepared in Example 1 to adjust the concentration of titanium oxide at 5% (w/v), and 10 mL of this solution was used for the following reaction. To the above dispersion was added 250 μL of 800 mM 1-ethyl-3-(3-diethylaminopropyl)carbodiimide and 500 μL of 100 mM N-hydroxysuccinic acid and a reaction was conducted while stirring at room temperature for 2 hours. The resulting solution was exchanged with a 10 mM HEPES buffer (pH 8.0) using a desalting column. To the resulting solution, 500 μL of a solution of adriamycin hydrochloride (SERVA) dissolved in DMSO at 2 mg/mL was added and reaction was conducted while stirring at 4° C. for 30 minutes. The reaction product was thoroughly dialyzed against PBS to obtain a dispersion liquid of titanium oxide nanoparticles coated with polyacrylic acid on which adriamycin is immobilized. The titanium oxide content obtained by the ash analysis as described in Example 1 was 3.67% (w/v).

The concentration of adriamycin was measured using free adriamycin as a reference and a fluorospectrophotometer (HITACHI F4010) at an excitation wavelength of 505 nm and a fluorescence wavelength of 575 nm. The adriamycin concentration of this dispersion liquid was 23.9 μg/mL. Accordingly, the adriamycin/titanium oxide ratio of this dispersion liquid was found to be 0.653 mg/g of titanium oxide.

Example 3

Evaluation of Safety of the Dispersion Liquid of Titanium Oxide Nanoparticle Coated with Polyacrylic Acid by Intravenous Injection Five to ten ICR mice (male, body weight: 30 to 35 g) were given one-shot intravenous injection of the polyacrylic acid-coated titanium oxide nanoparticle dispersion liquid that is described in Example 1 and had been buffer exchanged into PBS from the tail vein.

The results are shown in the following table. No mice died even after injection of 1 mL of the 1% (w/v) dispersion liquid, and safety of the dispersion liquid of titanium oxide nanoparticle coated with polyacrylic acid was thus established.

TABLE 1

|  | Dose (mL) | Titanium oxide concentration (mg/mL) | Titanium oxide concentration (%) | Total titanium oxide dose (mg) | Number of mice given administration (mice) | Number of dead mice (mice) | Safety (%) |
|---|---|---|---|---|---|---|---|
| Sample | 0.5 | 10 | 1 | 5 | 10 | 5 | 50 |
|  | 0.5 | 1 | 0.1 | 0.5 | 10 | 10 | 100 |
|  | 0.5 | 0.1 | 0.01 | 0.05 | 10 | 10 | 100 |
|  | 4 | 0.1 | 0.01 | 0.4 | 3 | 3 | 100 |
| PBS | 0.5 | 0 | 0 | 0 | 7 | 7 | 100 |
|  | 5 | 0 | 0 | 0 | 4 | 4 | 100 |

Example 4

Influence of Titanium Oxide Nanoparticles Coated with Polyacrylic Acid on which Adriamycin is Immobilized on Tumor Cells T24 cells derived from human bladder cancer in the logarithmic growth phase were cultured in an F-12 medium supplemented with 10% fetal bovine serum and inoculated to a 6 cm dish at about 100 cells/dish. The titanium oxide nanoparticles coated with polyacrylic acid on which adriamycin is immobilized prepared in Example 2 were added to the cells and the cells were cultured in a $CO_2$ incubator for 24 hours. After 24 hours, the cells were washed with PBS to remove the titanium oxide component and the F-12 medium supplemented with 10% fetal bovine serum was added. After the cells were cultured for 10 days, viable cells were counted by Giemza staining to determine colony-forming activity. Here, a PBS buffer was used as a control.

The results are shown in the following table.

The nanoparticles were found to exhibit cytotoxicity on cancer cells even at a concentration as low as about 10 μg titanium oxide/mL.

TABLE 2

| Final titanium oxide concentration (%) | Number of colonies | Colony forming activity (%) |
|---|---|---|
| 0.1 | 0 | 0 |
| 0.02 | 0 | 0 |
| 0.01 | 0 | 0 |
| 0.005 | 0 | 0 |
| 0.002 | 1.3 | 1.08 |
| 0.001 | 79.7 | 66.8 |
| 0.0005 | 116.6 | 97.7 |
| 0.0002 | 116.3 | 97.4 |
| 0.0001 | 114.3 | 9.8 |
| 0 | 119.3 | 100 |

Example 5

Study of Adverse Drug Reactions by Injection into the Oral Tissue of Rats

The dispersion liquid of titanium oxide nanoparticles coated with polyacrylic acid on which adriamycin is immobilized prepared in Example 2 was injected into the oral tissue of mice, and inflammation of the tongue was observed and body weight was measured to confirm adverse drug reactions to the particles.

The tongue of Wistar rats (male, 11-week-old, body weight 240 to 260 g) was fixed with forceps and 0.3 mL of the 0.005% (w/v) dispersion liquid of titanium oxide nanoparticles coated with polyacrylic acid on which adriamycin is immobilized was injected into the tongue. Black light at the strength of 2500 µW/cm² was immediately irradiated to the tongue for 30 minutes after the injection in one group (14 rats). No UV light treatment was given to another group.

Both groups were fed for 9 days in a normal manner to compare changes in body weight of surviving mice until Day 9. The results are shown in FIG. 2 and the following table.

TABLE 3

|  | No UV treatment | UV treatment |
| --- | --- | --- |
| Mortality | 6 | 0 |
| Mortality rate (%) | 43 | 0 |

When UV treatment was not conducted, 43% of the rats died. Since tumors were formed in the tongue of the rats due to an action of adriamycin bonded to the particle and the rats were unable to ingest feeds, their body weights decreased until Day 3.

In the group receiving UV irradiation, on the contrary, clear alleviation of inflammation was observed in a comparison conducted 5 hours after UV irradiation and only a trace of tumors remained 1 day after irradiation.

It was thus shown that cytotoxicity of adriamycin was completely eliminated by UV irradiation of about 30 minutes. In addition, the body weight scarcely decreased in the group receiving UV irradiation, and it was thus indicated that this treatment was very effective for reducing adverse drug reactions.

Example 6

Study of Antitumor Effect of Titanium Oxide Nanoparticles Coated with Polyacrylic Acid on which Adriamycin is Immobilized T24 cells derived from human bladder cancer were cultured using an F12 medium at 37° C. under 5.5% $CO_2$ gas atmosphere. The T24 cells were inoculated to a nude mice (BALV/c, male) to form a tumor. When the diameter of the tumor was about 5 to 7 mm, 200 µL of the 0.05% (w/v) titanium oxide nanoparticles coated with polyacrylic acid on which adriamycin is immobilized prepared in Example 2 was injected. As a control, a PBS solution was used and the same operation was conducted. After injection, UV light (2500 µW/cm²) was irradiated for 1 minute. The tumor volume of the nude mice was measured over 3 weeks. The results are shown in FIG. 3.

A superior antitumor effect was obtained by the titanium oxide nanoparticles coated with polyacrylic acid on which adriamycin is immobilized as compared to the control. In addition, the effect was suppressed by UV irradiation. The results conform to the above-described results that adriamycin was decomposed by the photocatalytic effect, and the titanium oxide nanoparticles coated with polyacrylic acid on which adriamycin is immobilized are quite effective in actual therapy.

Example 7

Preparation of a Dispersion Liquid of Titanium Oxide Nanoparticles Coated with Polyacrylic Acid on which Bleomycin is Immobilized Water was added to the polyacrylic acid-coated titanium oxide nanoparticles prepared in Example 1 to adjust a concentration of titanium oxide at 5% (w/v), and 10 mL of this solution was used for the following reaction. To the solution 250 µL of 800 mM 1-ethyl-3-(3-diethylaminopropyl)carbodiimide and 500 µL of 100 mM N-hydroxysuccinic acid were added and a reaction was conducted while stirring at room temperature for 2 hours. To the resulting solution 500 µL of a solution of bleomycin hydrochloride (Wako Pure Chemical Industries, Ltd.) dissolved in DMSO at 10 mg/mL was added and reaction was conducted while stirring at 4° C. for 30 minutes. The reaction product was thoroughly dialyzed against PBS to obtain a dispersion liquid of titanium oxide nanoparticles coated with polyacrylic acid on which bleomycin is immobilized. The titanium oxide concentration obtained by measurement of absorbance at 205 nm was 1.14% (w/v). The bleomycin potency of this dispersion liquid assayed by the paper method was 10.5 µg potency/mL. Accordingly, the bleomycin/titanium oxide ratio of this dispersion liquid was found to be 0.921 mg potency/g of titanium oxide.

Example 8

Influence of Titanium Oxide Nanoparticles Coated with Polyacrylic Acid On which Bleomycin is Immobilized on Tumor Cells The study was conducted as in Example 4, except that the titanium oxide nanoparticles coated with polyacrylic acid on which bleomycin is immobilized prepared in Example 8 were used in place of the titanium oxide nanoparticles coated with polyacrylic acid on which adriamycin is immobilized prepared in Example 2. The results are shown in the following table.

TABLE 4

| Final titanium oxide concentration (%) | Number of colonies | Colony forming activity (%) |
| --- | --- | --- |
| 0.114 | 0 | 0 |
| 0.0228 | 11.4 | 10.5 |
| 0.0114 | 43.4 | 40 |
| 0.00228 | 61.1 | 56.3 |
| 0.00114 | 86.8 | 80 |
| 0.000228 | 99.8 | 92 |
| 0.000114 | 110.5 | 100 |
| 0 | 108.5 | 100 |

Example 9

Figure 4:
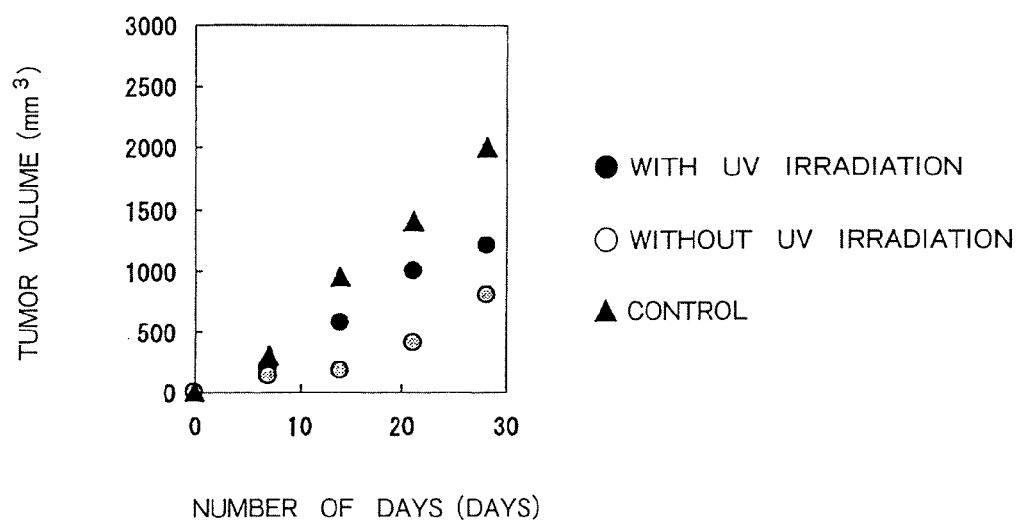
FIG. 4 shows the test results of an antitumor effect of titanium oxide nanoparticles coated with polyacrylic acid on which bleomycin is immobilized in Example 9.

Study of Antitumor Effect of the Titanium Oxide Nanoparticles Coated With Polyacrylic Acid on which Bleomycin is Immobilized The study was conducted as in Example 4, except that the titanium oxide nanoparticles coated with polyacrylic acid on which bleomycin is immobilized prepared in Example 8 were used in place of the titanium oxide nanoparticles coated with polyacrylic acid on which adriamycin is immobilized prepared in Example 2. The results are shown in FIG. 4.

Although present exemplary embodiments of the invention have been discussed above, it will be understood that variations and modifications may be made to the exemplary embodiments within the scope of the claims appended hereto.

What is claimed is:

1. A method of treating a lesion, comprising the steps of administering a dispersion to an animal including human wherein the dispersion comprises a titanium dioxide composite dispersed in an aqueous solvent where the titanium dioxide composite comprises a titanium dioxide particle, a hydrophilic polymer bonded to the surface of the titanium dioxide particle and a pharmaceutical compound bonded to the hydrophilic polymer, wherein the pharmaceutical compound is doxorubicin, the lesion is a cancer tissue and the amount of the doxorubicin is 0.5 to 5 mg per gram of the titanium dioxide particles wherein the titanium dioxide particle has a particle diameter of 2 to 200 nm, and subsequently irradiating with UV light a region other than the lesion at least surrounding the lesion, without irradiating the lesion, to photoexcite titanium dioxide in the titanium dioxide composite contained in the dispersion, so that the pharmaceutical compound is decomposed by photoexcitation of the titanium dioxide to allow the drug efficacy to disappear.

2. The method according to claim 1, wherein the hydrophilic polymer is a hydrophilic polymer having a carboxyl group bonded to a hydroxyl group on the surface of the titanium oxide particle by an ester bond.

3. The method according to claim 1, wherein the titanium dioxide particle has a particle diameter of 50 to 200 nm.

4. The method according to claim 1, wherein the titanium dioxide particle has an average particle diameter of about 20.2 nm.

* * * * *